United States Patent [19]
Ng

[11] Patent Number: 5,146,936
[45] Date of Patent: Sep. 15, 1992

[54] HAIR COLORING APPARATUS AND METHOD

[75] Inventor: Hilbert H. M. Ng, Chicago, Ill.

[73] Assignee: Charlene Products, Inc., Bolingbrook, Ill.

[21] Appl. No.: 558,652

[22] Filed: Jul. 26, 1990

[51] Int. Cl.$^5$ .............................................. A61K 7/13
[52] U.S. Cl. .................................... 132/208; 132/112; 132/116
[58] Field of Search ............... 132/108, 109, 110, 111, 132/112, 114, 116, 120, 129, 139, 151, 152, 153, 208, 219; 401/118, 119, 123, 36

[56] References Cited

U.S. PATENT DOCUMENTS

| | | | |
|---|---|---|---|
| 1,873,899 | 8/1932 | Mackenzie-Kennedy | 132/120 |
| 2,162,581 | 6/1939 | Kapelman | 132/120 |
| 2,660,182 | 11/1953 | Kaul | 132/109 |
| 2,761,459 | 9/1956 | Kaul | 132/109 |
| 3,424,176 | 1/1969 | Hale | 132/112 |
| 4,566,472 | 1/1986 | Mueller et al. | 132/110 |
| 4,691,720 | 9/1987 | Schmitz | 132/112 |

FOREIGN PATENT DOCUMENTS

| | | | |
|---|---|---|---|
| 951231 | 10/1956 | Fed. Rep. of Germany | 132/110 |
| 2133483 | 1/1973 | Fed. Rep. of Germany | 132/219 |
| 3341543 | 6/1985 | Fed. Rep. of Germany | 132/219 |

Primary Examiner—Gene Mancene
Assistant Examiner—Frank A. LaViola
Attorney, Agent, or Firm—Potthast & Ring

[57] ABSTRACT

A hair coloring apparatus (10) with a row of teeth members (14) and a plurality of applicator brushes (16) mounted for movement between an ingredient load position in which the application brushes are spaced from the row (14) of teeth (14), for immersion into a supply of coloring ingredient, to an application position in which the brushes are located between individual, selected pairs of adjacent teeth members (14) for coloring strands of hair which pass between only the selected pairs of teeth members (14) with loaded applicator members (16) located therebetween.

20 Claims, 2 Drawing Sheets

HAIR COLORING APPARATUS AND METHOD

BACKGROUND OF THE INVENTION

This invention relates to hair coloring apparatus, generally, and to a comb-like apparatus and method particularly adapted for selectively coloring narrow strands of hair to create a streak effect.

Various apparatus are known which employ comb-like devices with attached applicator members for applying hair coloring ingredient. In U.S. Pat. No. 2,660,182 issued Nov. 24, 1953 to Kaul and U.S. Pat. No. 1,704,492 issued Mar. 5, 1929 to Warren, rotary applicators are movably and fixedly mounted in side-by-side relation with respect to a comb to color all the hair passing through the comb. In U.S. Pat. No. 2,164,073 issued Jun. 27, 1939 to Madore a brush or removable wads of cotton at the back of a comb is used as the applicator for all the strands passing through the comb. Likewise, in U.S. Pat. No. 2,761,499 issued Sep. 4, 1956 to Kaul, a brush applicator is mounted for pivotal movement from a load position spaced from a pair of parallel combs to an application position in which it is located between a pair of combs and extend across all the teeth of the comb to color all the hair passing therethrough.

While these various apparatus function more or less successfully to color hair, they are not capable of functioning to selectively color only selected narrow strands of hair, since the applicators extend across the entire length of the associated comb structures rather than being capable of applying color only to selected strands of hair which pass through individual pairs of adjacent teeth members of the comb.

In U.S. Pat. No. 4,566,472 issued Jan. 28, 1986 of Mueller et al., color ingredient is provided in between selected adjacent pairs of teeth of the comb so that only selected strands of hair which pass between these selected pairs of teeth are colored. Unfortunately, instead of an applicator, the color ingredient is dispersed directly from a fluid holding chamber. Disadvantageously, the fluid holding chamber is fixedly attached to the comb and thus must be carefully filled with ingredient through use of a complicated and cumbersome procedure requiring a removable template to protect the comb from being contaminated with coloring ingredient at tooth locations at which no color is to be applied.

SUMMARY OF THE INVENTION

It is therefore the principal object of the present invention to provide a hair strand coloring apparatus in which less than all of the strands of hair which pass through the comb can be selectively colored as desired while providing a simple and convenient means and method for loading the applicator with coloring ingredient without the need for templates or the like to protect the comb against contamination. Generally, this objective is through provision of individual applicators between selected pairs of adjacent teeth of a comb which are movably mounted to the comb to enable simple loading of the applicators by means of immersion of the applicators into a supply of color ingredient.

In a preferred embodiment, a hair strand coloring apparatus is provided with a row of teeth members, at least one applicator member to hold and apply coloring ingredient to strands of hair which are contacted by the applicator member and means for mounting the row of teeth members and the at least one applicator member for relative movement between an application position and a load position. In the application position at least one applicator member resides between a pair of adjacent teeth members for application of liquid ingredient to hair passing only between said pair of teeth. In the ingredient load position the at least one applicator member is spaced from between the pair of adjacent teeth sufficiently to enable its immersion into liquid ingredient without immersing the row of teeth members.

Thus, a method of applying hair coloring ingredient to only selected, relatively narrow strands of hair using a comb in combination with a hair coloring applicator member movably attached to the comb is also provided. According to the invention, this method preferably comprises the steps of immersing the applicator member into a source of hair coloring ingredient to hold and apply the ingredient to a strand of hair, moving the applicator to an application position in which it resides between a pair of adjacent teeth of the comb less than all of the pairs of teeth of the comb and passing the comb through a person's hair to apply ingredient to only the hair strands which pass between the pair of adjacent teeth between which the applicator resides.

BRIEF DESCRIPTION OF THE DRAWINGS

The foregoing objects and advantageous features of the invention will be explained in greater detail and others will be made apparent from the claims and the detailed description of the preferred embodiment of the present invention which is given with reference to the several figures of the drawing, in which:

DETAILED DESCRIPTION

Figure 1:
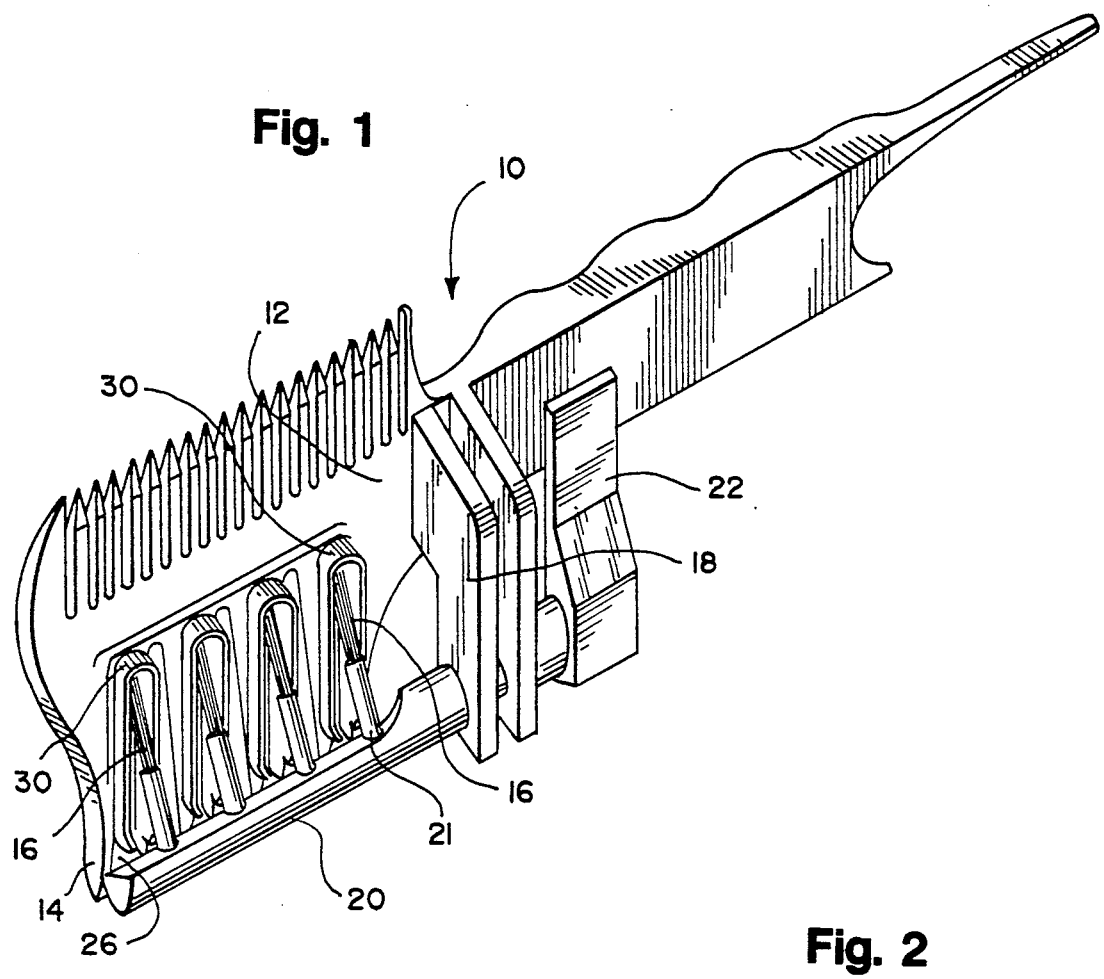
FIG. 1 is a perspective view of the hair coloring apparatus.
Figure 3:
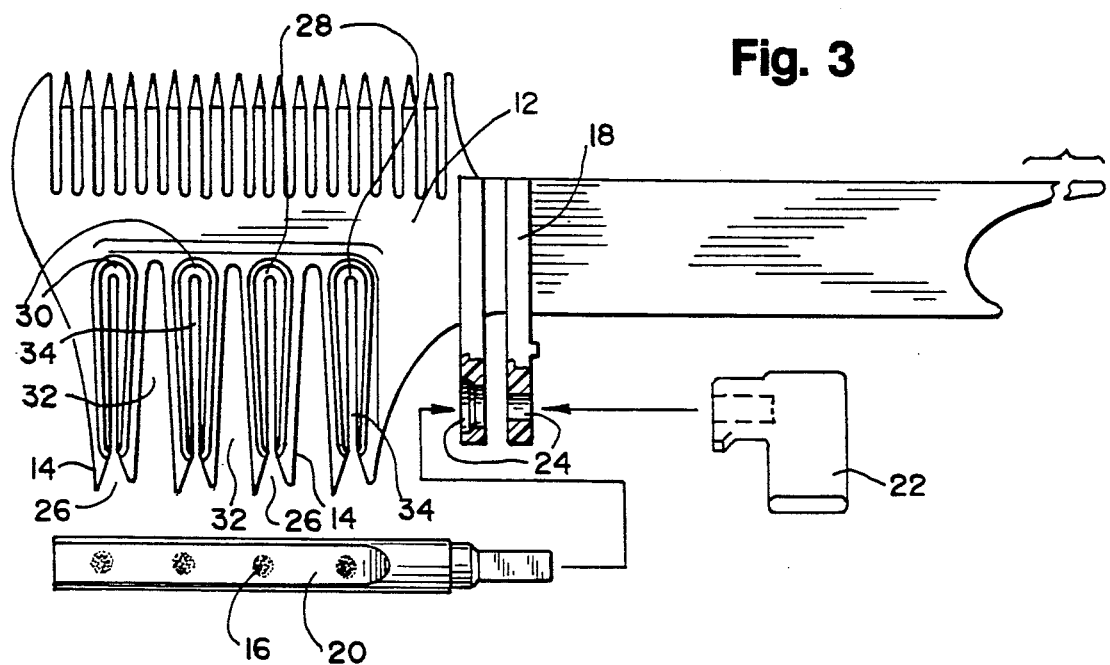
FIG. 3 is a profile view of the hair coloring apparatus as shown in FIG. 2.
Figure 1A:
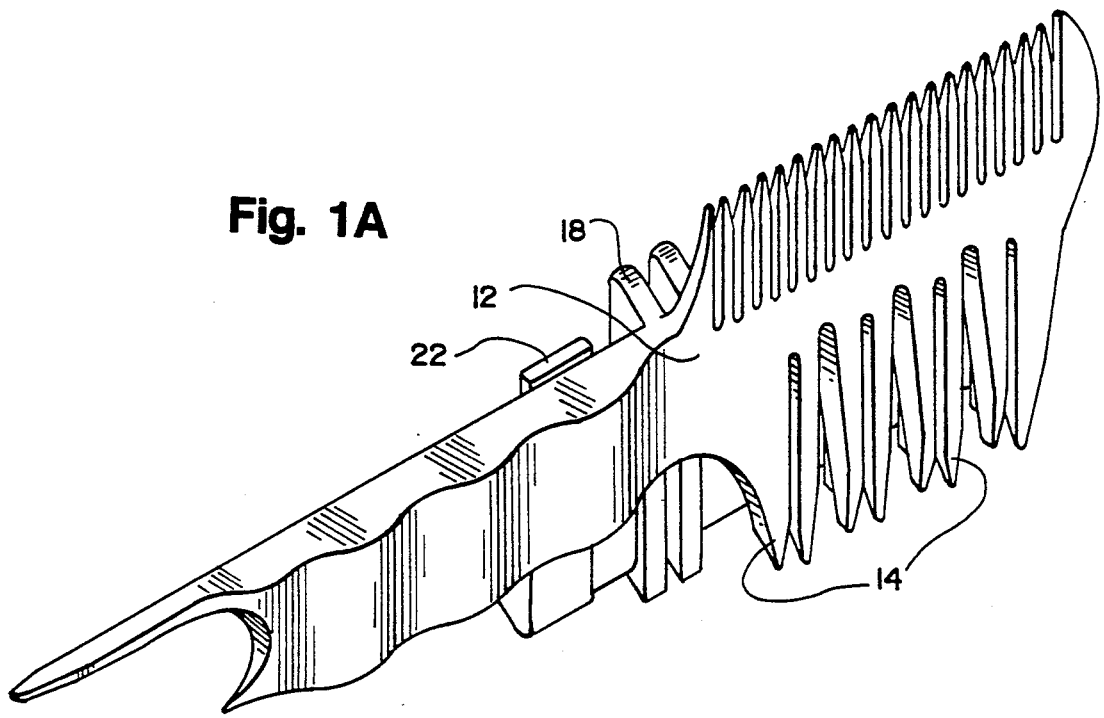
FIG. 1A is a perspective view of the back side of the hair coloring apparatus shown in FIG. 1.

Referring now to these drawings, this hair strand coloring apparatus 10 which is used to provide ease in color streaking hair, comprises, as seen in FIG. 1, a body 12 having a row of teeth members 14, seen also in FIGS. 1A and 3. Adjacent the row of teeth members 14 are applicator members 16. Members 16 comprise narrow brushes, or the like, which are able to hold a coloring ingredient and apply it to strands of hair that come into contact with members 16.

Body 12, pivot axle mounting bracket 18 and means for mounting applicator members or 21 on pivot axle 20 to which the applicator members 16 are mounted, comprise a means for mounting applicator members 16 for relative lateral movement between teeth 14 and applicator members 16.

Applicator member 16, when holding a color ingredient and is residing between a pair of adjacent teeth members 14, are in an application position, as seen in FIG. 1. Applicator members 16, being disposed between a pair of adjacent teeth 14, will deposit coloring ingredient to strands of hair that come through the pair of teeth 14 in which such an applicator member 16 is residing.

Figure 2:
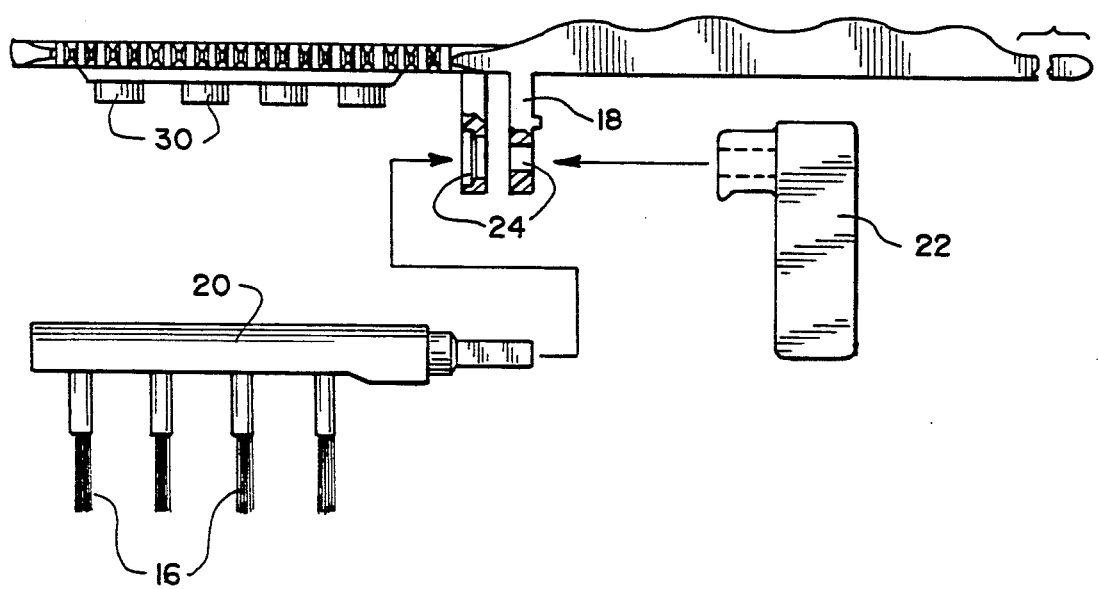
FIG. 2 is a top view of FIG. 1 which is fragmented, partially cut away and exploded.

Once the applicator members 16 have dispensed with the coloring ingredient, the applicator members 16 are rotated away from teeth members 14. This is accomplished by moving manually actuatable member or thumb member 22 away from body 12. Since thumb member 22 is connected to and laterally extending from pivot axle 20, which in turn is mounted to pivot axle mounting bracket 18 through its axle holding apertures 24, as seen in FIGS. 2 and 3, as thumb member 22 is pushed away from body 12, applicator members 16 will likewise move away from teeth 14. Once applicator members 16 are moved sufficiently away from teeth members 14, they are then in a color ingredient load position. Applicator members then can be immersed into a coloring ingredient without having any teeth members 14 becoming immersed. By not permitting teeth members 14 to be immersed into the ingredient, undesired application of the color ingredient can be avoided. Thus, hair in line with and in contact with applicator members 16 will only be colored, thereby, obtaining precise desired streak coloring.

As one can readily see mounting means or pivotal axis 20 holds all of applicator members 16 in relative alignment with each other, thereby providing simultaneous movement of the applicator members 16 from an application position to an ingredient load position. The applicator members 16 are spaced apart from one another and each are aligned to be between different adjacent pairs of teeth 14 when in an application position, as seen in FIG. 1. There should be more pairs of adjacent teeth members 14 than applicator members 16, to inpart streaking of the hair. Thus, hair that passes through a pair of adjacent teeth 14 where an applicator member 16 is not located, does not receive color ingredient.

In the present embodiment, the pivot axle 20 is mounted adjacent open portions 26 of teeth members 14, as seen in FIGS. 1 and 3, and is laterally spaced and substantially parallel to the row of teeth 14, as can be seen in FIGS. 1 and 2. This spacing prevents hair, which passes through teeth members 14, from getting caught between teeth members 14 and pivot axle 20.

When applicator members 16 are in an application position, as seen in FIG. 1, members 16 are held in that position by the hairdresser's thumb applying pressure to thumb member 22. Pressure is applied in an upward direction, causing members 16 to contact a blocking means or blocking member 28 as seen in FIG. 3. Since pivot axle 20 is spaced apart from teeth 14, when members 16, being elongate, are in contact with blocking member 28, as seen in FIG. 1, creating an acute angle between members 16 and teeth 14. Blocking member 28 is an arch wall which separates a pair of adjacent teeth into having a front and back side. The opening between adjacent teeth members 14, which will have an applicator member 16 residing when in an application position, has a relatively wider opening defined by wall member 30 on the side the applicator member 16 is located, as seen in FIGS. 1 and 3, than the opening defined by blocking member 28 which is carried through to the opposite side of teeth 14, as seen in FIGS. 2 and 1A.

In this embodiment, as seen in FIG. 3, gap 32 between adjacent teeth members 14, in which no applicator member will be positioned, is wider than opening 34 which will contain applicator member 16 when in the application position.

This new device is very simple and easy to use for applying color ingredient to desired strands of hair in a streaking configuration. The operator simply immerses applicator members 16 into a source of hair coloring ingredient. Immersing members 16 into the ingredient will cause the ingredient to be held to member 16 when it is removed from the ingredient. Once it is held to members 16, the color ingredient can be applied to desired strands of hair. Once members 16 are holding the coloring ingredient, members 16 are moved to an application position, as seen in FIG. 1. This application position is placing member 16 between two adjacent teeth members 14. There will be less applicator members 16 than gaps created by adjacent teeth members 14. This is necessary in order to impart a streaking pattern of the color. The comb is then passed through the hair thereby applying color ingredient only to strands of hair which pass through a pair of adjacent teeth members 14 which have an applicator member 16 residing therebetween. This will thereby easily apply color ingredient in a streak fashion to a desired section of hair.

The moving of the applicator members 16 away from teeth members 14 permits immersion of members 16 into the color ingredient without teeth members 14 being immersed. This provides precise application of color ingredient by members 16 only and not by any other portion of the comb.

In moving thumb member 22, the operator pivotally moves applicator members 16 laterally away or toward the comb teeth members 14. The operator, as a result, can easily operate this device with one hand.

With the applicator members 16 in an application position, as seen in FIG. 1, the apparatus is pulled through a section of hair in which the hair comes through the teeth members 14 from the opposite side members 16 are located on.

This apparatus can be easily disassembled, as seen in FIG. 3, thumb member 22 can be pulled apart from pivot axle 20. Once these two parts are pulled apart, members 16 and axle 20 can be cleaned to remove color ingredient after use, and then can be easily reattached by pushing their mating members together.

This releasable detaching of axle 20 which holds members 16, permits an operator to easily replace the applicator member with another.

While a detailed description of the preferred embodiment of the invention has been given, it should be appreciated that many variations can be made thereto without departing from the scope of the invention as set forth in the appended claims.

I claim:

1. A hair strand color apparatus, comprising:
  a row of teeth members;
  at least one applicator member to hold and apply coloring ingredient to strands of hair which are contacted by the applicator member; and
  means for mounting the row of teeth members and at least one applicator member for relative movement therebetween
  an application position in which at least one applicator member resides entirely between and is spaced at a distance away from a pair of adjacent teeth members for application of liquid ingredient to hair passing only between said pair of teeth; and
  an ingredient load position in which the at least one applicator member is spaced from between the pair of adjacent teeth sufficiently to enable its immersion into liquid ingredient without immersing the row of teeth members.

2. The hair coloring apparatus of claim 1 including a plurality of applicator members, and in which
  said mounting means includes means for mounting all of said plurality of applicator members for simultaneous movement between the application position and the ingredient load position, each of said applicator members being moved to a position between different pairs of teeth members.

3. The hair coloring apparatus of claim 1 in which there are more pairs of teeth members in the row of teeth members than there are applicator members.

4. The hair coloring apparatus of claim 1 in which said relative movement mounting means mounts the row of teeth members and the at least one applicator member for relative lateral movement therebetween.

5. The hair coloring apparatus of claim 4 in which said relative movement mounting means includes a pivot axle for mounting the at least one applicator member for pivotal movement relative to the row of teeth members.

6. The hair coloring apparatus of claim 5 in which said mounting means includes means for mounting said pivot axle adjacent an open edge of the row of teeth members.

7. The hair coloring apparatus of claim 5 in which said mounting means includes means for mounting said pivot axle laterally spaced from but substantially parallel to the row of teeth members.

8. The hair coloring apparatus of claim 5 including a manually actuatable member attached to and extending laterally from the pivot axle to facilitate pivotal movement of the at least one applicator member relative to the row of teeth members.

9. The hair coloring apparatus of claim 1 in which the at least one applicator member comprises an elongate, relatively narrow brush.

10. The hair coloring apparatus of claim 1 in which said at least one applicator member is an elongate member which extends between the pair of adjacent teeth members at an acute angle relative to the teeth members.

11. The hair coloring apparatus of claim 1 including means associated with the pair of adjacent teeth members for blocking further movement of at least the one applicator member beyond the application position.

12. The hair coloring apparatus of claim 11 in which said blocking means is a blocking member between the pair of adjacent teeth and lying in the path of movement of the applicator member to engage it and thereby block its further movement.

13. The hair coloring apparatus of claim 1 in which at least one other pair of adjacent teeth members defines an opening substantially wider than a gap defined by said pair of adjacent teeth members between which said at least one applicator member resides when in the application position.

14. The hair coloring apparatus of claim 13 in which the row of teeth members has a pair of opposite sides said at least one applicator member is moved in between the pair of adjacent teeth members defining an opening from one of said opposites sides, and a relatively narrower opening is defined by said pair of adjacent teeth members on the other of said opposite sides.

15. A method of applying hair coloring ingredient to only selected, relatively narrow strands of hair using a comb in combination with a hair coloring applicator member movably attached to the comb, comprising the steps of:

immersing the applicator member into a source of hair coloring ingredient to hold and apply the ingredient to a strand of hair;

moving the applicator member to an application position in which it resides entirely between and spaced at a distance away from a pair of adjacent teeth of the comb less than all of the pairs of teeth of the comb;

passing the comb through the person's hair to apply ingredient to only the hair strands which pass between the pair of adjacent teeth between which the applicator resides.

16. The method of claim 15 including the step of moving the applicator member away from the comb to enable performance of said step of immersing without immersing the comb into the ingredient.

17. The method of claim 15 in which said step of moving includes the step of manually moving a thumb member to pivotally move the applicator member laterally toward the comb into the application position.

18. The method of claim 15 in which said comb has a pair of opposite sides, said step of moving includes the step of moving the applicator member to the application position from one of said opposite sides, and said step of passing a comb through the hair of a person is performed from the other one of said opposite sides of the comb.

19. The method of claim 15 including the steps of detaching the applicator member from the comb, cleaning the applicator member while detached, and reattaching the applicator member to the comb for movement relative thereto.

20. The method of claim 15 including the steps of releasably detaching the applicator member from the comb, and attaching in its place, another substantially identical, applicator member.

* * * * *

UNITED STATES PATENT AND TRADEMARK OFFICE
CERTIFICATE OF CORRECTION

PATENT NO. : 5,146,936
DATED : September 15, 1992
INVENTOR(S) : Hilbert H. M. Ng It is certified that error appears in the above-identified patent and that said Letters Patent is hereby corrected as shown below:

Col. 2, line 53, delete "or"

Signed and Sealed this

Fifth Day of October, 1993

Attest:

BRUCE LEHMAN

*Attesting Officer*     Commissioner of Patents and Trademarks